Dec. 26, 1961 E. S. BOERNER Plant Pat. 2,113
ROSE PLANT
Filed Feb. 7, 1961
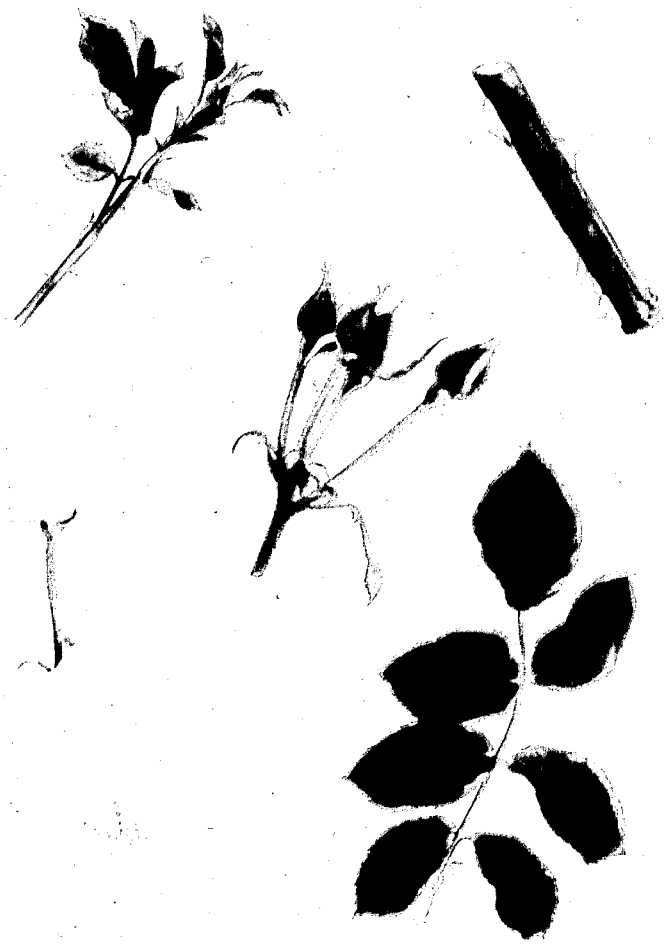
Inventor.
E. S. Boerner
By: Robb & Robb
Attorneys.

United States Patent Office

Plant Pat. 2,113
Patented Dec. 26, 1961

2,113
ROSE PLANT

Eugene S. Boerner, Newark, N.Y., assignor, by mesne assignments, to Home Nursery Products Corporation, Newark, N.Y., a corporation of New York Filed Feb. 7, 1961, Ser. No. 87,725
1 Claim. (Cl. 47—61)

The present invention relates to a new and distinct variety of rose plant of the floribunda class, which was originated by me by crossing an unnamed and unpatented seedling derived from a cross of "Goldilocks" (Plant Patent No. 672) × "Pinocchi" (Plant Patent No. 484) with the variety "Vogue" (Plant Patent No. 926).

The primary objective of this breeding was to produce a new rose variety in which the plant habit is more upright and the plant is of larger size while retaining the floriferous habit of the unnamed parent seedling. This objective was fully achieved, along with other desirable improvements, as evidenced by the following unique combination of characteristics which are outstanding in the new variety and which distinguish it from its parents, as well as from all other varieties of which I am aware:

(1) Large, upright and floriferous habits of growth;
(2) Abundant foliage;
(3) A long-lasting flower quality;
(4) A distinctive and attractive general color tonality of the flowers corresponding to Eosine Pink, lightly overcast with La France Pink, with the lower half of the flower petals lightly overcast with Barium Yellow from the base of the flower; and
(5) An unusual and strong spicy fragrance of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Goldilocks" × "Pinocchio."
*Pollen parent.*—"Vogue."
Classification:
*Bontanic.*—Floribunda.
*Commercial.*—Floribunda.

*Flower*

(Observations made from specimens grown outdoors at Newark, New York, in the early morning during the middle part of the month of August.)

Blooming habit: Recurrent—continuous.
Bud:
*Size.*—Small.
*Form.*—Ovoid; is not affected by wet or hot weather.
*Color.*—When, sepals first divide—Venetian Pink Plate 13. When petals begin to unfurl—Peach Red, Plate 1. When half-blown: inside of petals—Eosine Pink, Plate 1, lightly overcast with Geranium Pink, Plate 1; reverse of petals—Pale Orange Yellow, Plate 3, lightly overcast with Eosine Pink, Plate 1.
*Sepals.*—Slightly branched; curl back when petals begin to unfurl. Color: inside—Absinthe Green, Plate 31; outside—Biscay Green, Plate 17, with edges overcast with Victoria Lake, Plate 1.
*Calyx.*—Color—Light Bice Green, Plate 17. Shape—pear. Size—slender. Aspect—smooth. Odor when rubbed—none.
*Peduncle.*—Length—short. Aspect—rough. Strength—erect; slender. Color—Light Hellebore Green, Plate 17.
*Opening.*—Opens up well; is not affected by adverse weather conditions.
Bloom:
*Size.*—Medium. Average size when fully expanded—3 inches.
*Borne.*—Both singly and several together.
*Stems.*—Medium length; strong.
*Form* (when first open).—Cupped. Permanence—retains its form to the end.
*Petalage.*—Double (full but open center). Number of petals under normal conditions—from 30 to 35.
*Color.*—Center of flower—Eosine Pink, Plate 1. Outer petals—La France Pink, Plate 1, lightly overcast with Eosine Pink, Plate 1, with lower half of petals overcast with Massicot Yellow, Plate 16, from the base. Base of petals (aiglet)—Pinard Yellow, Plate 4. Inside of petals—Eosine Pink, Plate 1, lightly overcast with La France Pink, Plate 1, with the lower half of the petals lightly overcast with Barium Yellow, Plate 16, from the base. Reverse of petals—La France Pink, Plate 1, lightly overcast with Cameo Pink, Plate 26, in the lower half of the petals. General tonality from a distance—Eosine Pink, Plate 1.
*Discoloration.*—General tonality at end of first day—Eosine Pink, Plate 1. Second day—Eosine Pink, Plate 1. Third day—Eosine Pink, Plate 1, lightly overcast with La France Pink, Plate 1.
Petals:
*Texture.*—Leathery; is not affected by wet or hot weather.
*Appearance.*—Inside—satiny . Outside—shiny.
*Form.*—Round.
*Arrangement.*—Imbricated (regularly arranged shingle-like).
*Petaloids in center.*—Few; large.
*Persistence.*—Drop off cleanly.
*Fragrance.*—Strong. Nature—spicy.
*Lasting quality.*—On the plant—long. As cut flower—long.

*Genital organs*

Stamens, anthers: Small; many; regularly arranged around styles. Color—Orange—Buff, Plate 3.
Stamens, filaments (threads): Medium length. Color—Baryta Yellow, Plate 4.
Pollen: Color—Pale Yellow-Orange, Plate 3.
Styles: Columnar; uneven length; medium length; thin.
Stigmas: Color—Straw Yellow, Plate 16.
Ovaries: All enclosed in calyx.
Hips: None.
Seeds: None.

*Plant*

Form: Bush.
Growth: Vigorous; upright.
Foliage: Compound of 3–7 leaflets.
*Size.*—Small.
*Quantity.*—Abundant.
*Color.*—New foliage: upper side—Hay's Maroon, Plate 13; under side—Van Dyke Red, Plate 13. Old foliage: upper side—Varley's Green, Plate 18; under side—Jade Green, Plate 31.

*Shape.*—Oval pointed.

*Texture.*—Upper side—leathery; glossy. Under side—smooth.

*Ribs and veins.*—Ordinary.

*Edge.*—Serrated (saw toothed).

*Serration.*—Both double and single; small.

*Leaf stem.*—Color—Cress Green—Plate 31. Under side—prickly.

*Stipules.*—Short; slightly bearded.

Wood:

*New wood.*—Color—Courge Green, Plate 17, lightly overcast with Acajou Red, Plate 13. Bark—smooth.

*Old wood.*—Color—Varley's Green, Plate 18. Bark, smooth.

Thorns:

*Thorns.*—Quantity: on main stalks from base—ordinary; on laterals from stalk—ordinary. Form—flat base; medium length; hooked downward.

Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of upright, large size and floriferous habits of growth, abundant foliage, long-lasting flower qualities, a distinctive and attractive general color tonality of the flowers corresponding to Eosine Pink, lightly overcast with La France Pink, and with the lower half of the flower petals lightly overcast with Barium Yellow from the base, and an unusual, strong and spicy fragrance of the flowers.

No references cited.